(12) United States Patent
Cable et al.

(10) Patent No.: US 9,366,651 B2
(45) Date of Patent: Jun. 14, 2016

(54) ARRAY OF SENSORS WITH SURFACE MODIFICATIONS

(71) Applicant: MATRIX SENSORS, INC., San Diego, CA (US)

(72) Inventors: Michael D Cable, Danville, CA (US); Heinrich Sussner, Palo Alto, CA (US); Steven Yamamoto, San Diego, CA (US)

(73) Assignee: MATRIX SENSORS, INC., San Diego, CA (US)

( * ) Notice: Subject to any disclaimer, the term of this patent is extended or adjusted under 35 U.S.C. 154(b) by 21 days.

(21) Appl. No.: 14/322,756

(22) Filed: Jul. 2, 2014

(65) Prior Publication Data

US 2015/0011428 A1 Jan. 8, 2015

Related U.S. Application Data

(60) Provisional application No. 61/842,821, filed on Jul. 3, 2013.

(51) Int. Cl.
| | |
|---|---|
| *G01N 15/06* | (2006.01) |
| *G01N 33/00* | (2006.01) |
| *G01N 33/48* | (2006.01) |
| *G01N 29/02* | (2006.01) |
| *G01N 29/028* | (2006.01) |
| *G01N 29/036* | (2006.01) |
| *G01N 29/24* | (2006.01) |

(52) U.S. Cl.
CPC ............ *G01N 29/022* (2013.01); *G01N 29/028* (2013.01); *G01N 29/036* (2013.01); *G01N 29/2406* (2013.01); *G01N 33/0031* (2013.01); *G01N 2291/0427* (2013.01); *G01N 2291/106* (2013.01)

(58) Field of Classification Search
CPC ........ G01N 15/06; G01N 33/00; G01N 33/48
USPC ............... 422/50, 68.1, 83, 82.01, 98; 436/43
See application file for complete search history.

(56) References Cited

U.S. PATENT DOCUMENTS

| | | | |
|---|---|---|---|
| 7,105,301 B2 | 9/2006 | Su | |
| 7,305,883 B2 * | 12/2007 | Khuri-Yakub et al. | ......... 73/579 |
| 8,105,780 B2 * | 1/2012 | Su et al. | ....................... 435/6.11 |
| 8,367,314 B2 | 2/2013 | Chilkoti | |
| 8,449,824 B2 | 5/2013 | Sun | |
| 2002/0128234 A1 | 9/2002 | Hubbell | |
| 2005/0244820 A1 * | 11/2005 | Su et al. | ........................... 435/5 |
| 2006/0257919 A1 | 11/2006 | Frutos | |

(Continued)

*Primary Examiner* — Brian J Sines
(74) *Attorney, Agent, or Firm* — Mark B. Floyd

(57) ABSTRACT

Surface modifications to sensors in an array give the sensors different functionalities for adsorbing or binding molecules. A first sensor in the array includes a first resonating member having a first surface comprising a receptor material coated over a first underlying material. A second sensor includes a second resonating member having a second surface comprising the receptor material coated over a second underlying material that is different than the first underlying material. The first underlying material, the second underlying material, and the receptor material are selected such that the first resonating member, having a combination of the receptor material and the first underlying material, has a different ability to adsorb or bind a mass of one or more analytes than does the second resonating member having a combination of the receptor material with the second underlying material. Methods for fabricating sensors with surface modifications are also provided.

9 Claims, 9 Drawing Sheets

(56) References Cited

U.S. PATENT DOCUMENTS

| | | | |
|---|---|---|---|
| 2008/0156100 A1* | 7/2008 | Hines | 73/584 |
| 2011/0019186 A1* | 1/2011 | Himmelhaus et al. | 356/317 |
| 2013/0098141 A1* | 4/2013 | McCaig et al. | 73/24.06 |

* cited by examiner

ARRAY OF SENSORS WITH SURFACE MODIFICATIONS

CROSS REFERENCE TO RELATED APPLICATIONS

This application claims the benefit of U.S. provisional patent application 61/842,821 filed on Jul. 3, 2013, titled "Array of Sensors with Surface Modifications", which application is hereby incorporated by reference in its entirety.

BACKGROUND

The invention relates to sensor arrays for detecting analytes, and in particular to an array of sensors with surface modifications to change sensor responses to analytes.

Resonant sensors use target molecules adsorbed in a sensing material to change properties that are reflected in the resonance frequencies of the sensors. A wide variety of cantilever, membrane and piezoelectric resonator-based sensors have been fabricated using MEMS technology. These sensors generally detect agents through the use of polymer films and coatings with selective adsorption for a specific agent or set of agents. Although these sensors provide a certain degree of sensitivity, it is desirable in many applications to have sensors with even higher sensitivities.

A capacitive micromachined ultrasonic transducer (cMUT) is a micromachined device having a substrate and a membrane supported above the substrate by an insulating material. A variable voltage applied between the substrate and membrane drives the membrane to vibrate and emit sound waves at ultrasonic frequencies. Arrays of cMUTs have been used for transmitting and receiving ultrasonic beam patterns in air and water over a frequency range from 10 kHz to 100 MHz. These cMUTs rely on the very large electric field in the gap of the capacitor to provide an electromechanical coupling coefficient close to unity.

cMUTs are mostly used for medical imaging. In addition, they have been used to indirectly measure various fluid characteristics, based on processing of ultrasonic signals transmitted and received through the fluid. In current cMUT devices and applications, the cMUT elements are used to transmit and/or receive ultrasonic energy between the cMUT element and the environment. Moreover, to ensure reliable and consistent operation, cMUT element membranes are normally designed to be non-reactive to chemicals, light, and other environmental factors that may alter or interfere with their operational characteristics. However, due to their resonant character, cMUT devices have the potential to be used as sensors, in a manner similar to MEMS cantilever, membrane, and piezoelectric resonator-based sensors.

One use of cMUT devices in an array of sensors is disclosed in U.S. Pat. No. 7,305,883 to Khuri-Yakub. Sensor elements include a functionalized membrane supported over a substrate by a support frame. The sensor element is connected to an electrical circuit, which is configured to operate the sensor element at or near an open circuit resonance condition. The mechanical resonance frequency of the functionalized membrane is responsive to binding of an agent to the membrane. The exterior surface of each sensor membrane is chemically functionalized to have an affinity for one or more specific, predetermined chemicals. A detector provides a sensor output responsive to the mechanical resonance frequency of the sensor element. A potential disadvantage to this approach is that it may be difficult, time consuming, and/or expensive to chemically functionalize each membrane in the array with different polymer materials to attract different analytes. This is difficult due to the tiny size of the membranes and the limitations of droplet technology for placing drops of different polymers on the membranes to adsorb or bind different target molecules.

US patent application 20130098141 to McCaig discloses cantilever chemical vapor sensors. The sensors are tailored to respond in frequency by controlling the location of deposition of an adsorbing layer, using a gold layer to promote deposition of the adsorbing layer of a polymeric material in a desired location. A thin film of chromium is deposited by thermal evaporation on regions of the device where polymer film growth is to be suppressed or inhibited. Electron beam lithography is used to pattern the chromium masking layer on top of the gold layer before the cantilevers are suspended using a plasma etch. Localization of polymer coating is achieved utilizing a combination of surface initiated atom transfer polymerization (SI-ATRP) and disulfide self-assembled monolayer (SAM) formation on gold. The polymerization initiator contains a disulfide which will adhere to the gold surface, and polymerization only occurs (or very preferentially occurs) at those locations. SI-ATRP is then used to grow a polymer film which is localized to the bare gold surface.

SUMMARY

According to an aspect, a device comprises at least first and second resonator sensors. The first sensor includes a first resonating member having a first surface comprising a receptor material coated over a first underlying material. The second sensor includes a second resonating member having a second surface comprising the receptor material coated over a second underlying material that is different than the first underlying material. The first underlying material, the second underlying material, and the receptor material are selected such that the first resonating member, having a combination of the receptor material and the first underlying material, has a different ability to adsorb or bind a mass of one or more analytes than does the second resonating member having a combination of the receptor material with the second underlying material. The device also comprises at least one detector for detecting responses of the sensors when the sensors are exposed to a sample potentially containing one or more of the analytes.

According to another aspect, a method is provided for modifying surfaces of a plurality of resonator sensors in an array. The resonator sensors have respective resonating members for detecting one or more analytes. The method comprises patterning a first coating material on at least one of the sensors such that the first coating material coats at least one of the resonating members and such that at least one of the resonating members is not coated with the first coating material. Then a receptor material is coated on substantially all of the resonating members in the array. The first coating material and the receptor material are selected such that the at least one resonating member that is coated with a combination of the first coating material and the receptor material has a different ability to adsorb or bind a mass of one or more of the analytes than does the at least one resonating member that is coated with the receptor material without the first coating material.

According to another aspect, a method is provided for modifying surfaces of at least first and second resonator sensors. The resonator sensors have respective first and second resonating members, and the method comprises depositing and patterning a first coating material such that the first coating material coats the first resonating member and does not coat the second resonating member. The method also comprises depositing and patterning a second coating material such that the second coating material coats the second resonating member and does not coat the first resonating member. The method further comprises coating both the first and second resonating members with a receptor material that covers the first and second coating materials. The first and second coating materials and the receptor material are selected such that the first resonating member that is coated with a combination of the receptor material covering the first coating material has a different ability to adsorb or bind a mass of one or more analytes than does the second resonating member that is coated with a combination of the receptor material covering the second coating material.

BRIEF DESCRIPTION OF THE DRAWINGS

The foregoing aspects and advantages of the present invention will become better understood upon reading the following detailed description and upon reference to the drawings where.

DETAILED DESCRIPTION OF PREFERRED EMBODIMENTS

In the following description, it is understood that all recited connections between structures can be direct operative connections or indirect operative connections through intermediary structures. A set of elements includes one or more elements. Any recitation of an element is understood to refer to at least one element. A plurality of elements includes at least two elements. Unless otherwise required, any described method steps need not be necessarily performed in a particular illustrated order. A first element (e.g. data) derived from a second element encompasses a first element equal to the second element, as well as a first element generated by processing the second element and optionally other data. Making a determination or decision according to a parameter encompasses making the determination or decision according to the parameter and optionally according to other data. Unless otherwise specified, an indicator of some quantity/data may be the quantity/data itself, or an indicator different from the quantity/data itself. Computer programs described in some embodiments of the present invention may be stand-alone software entities or sub-entities (e.g., subroutines, code objects) of other computer programs. Computer readable media encompass non-transitory media such as magnetic, optic, and semiconductor storage media (e.g. hard drives, optical disks, flash memory, DRAM), as well as communications links such as conductive cables and fiber optic links According to some embodiments, the present invention provides, inter alia, computer systems comprising hardware (e.g. one or more processors and associated memory) programmed to perform the methods described herein, as well as computer-readable media encoding instructions to perform the methods described herein.

The following description illustrates embodiments of the invention by way of example and not necessarily by way of limitation.

Figure 1:
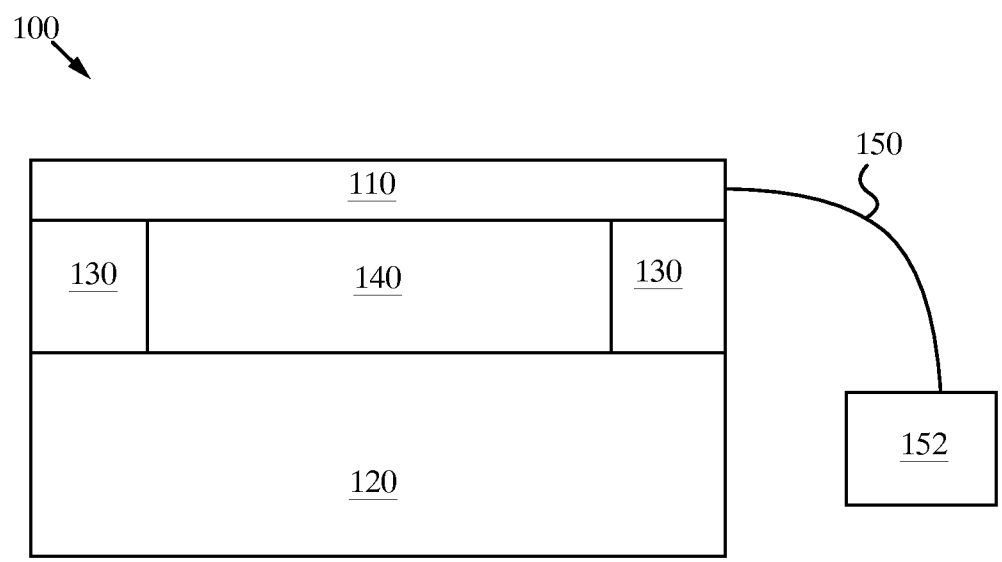
FIG. 1 shows a schematic, cross-sectional view of a sensor according to one embodiment of the invention.

FIG. 1 is a schematic, cross-sectional diagram of a resonator sensor, according to some embodiments of the invention. Resonator sensors include, without limitation, capacitive micromachined ultrasonic transducer (cMUT), cantilever, and piezoelectric resonator-based sensors. FIG. 1 shows a cMUT sensor 100 that has a functionalized membrane 110, which is functionalized with a receptor material for adsorbing or binding one or more analytes. Functionalized membrane 110 is supported over a substrate 120 by support frame 130. Functionalized membrane 110, support frame 130 and substrate 120 define a vacuum gap 140. Vacuum gap 140 is preferably between about 0.1 µm and about 0.5 µm in height. The sensor 100 is connected to a detector 152 through a connector 150. In general, the detector 152 preferably employs a detection modality to measure a sensor response to one or more analytes (e.g., a change in the position or resonance frequency of the membrane 110). In preferred embodiments, the detector 152 detects a resonance frequency of the functionalized membrane 110, which frequency may change during exposure to one or more analytes. Suitable detectors include, but are not limited to, an optical detector, a mechanical stress detector, a magnetic detector, and a capacitance detector.

In one embodiment, functionalized membrane 110 is driven thermally (by applied heat or by thermal noise) or electrically, and an optical detector is used to detect deflection or resonant frequency shifts of functionalized membrane 110. Interferometric optical detection techniques are described in U.S. Pat. No. 6,567,572, by Degertekin et al., which is incorporated herein by reference. In other embodiments, functionalized membrane 110 has thin piezoelectric or magnetic films that provide coupling. The resonant functionalized membranes 110 may be addressed by capacitor action (cMUTs), by a piezoelectric thin film (pMUTs), or by a magnetic film on the surface (mMUTs). Alternatively, a change in membrane deformation may be detected directly through a change in impedance, capacitance, magnetic field, piezoelectric signal, change in resistance through the piezoresistive effect, or optically using an interferometer, or any other detection modality to measure the response of sensor 100 to exposure to one or more analytes in a sample. Preferably, functionalized membrane 110 operates at a mechanical resonance frequency of at least about 1 MHz, more preferably between about 1 MHz and about 100 MHz.

Figure 2:
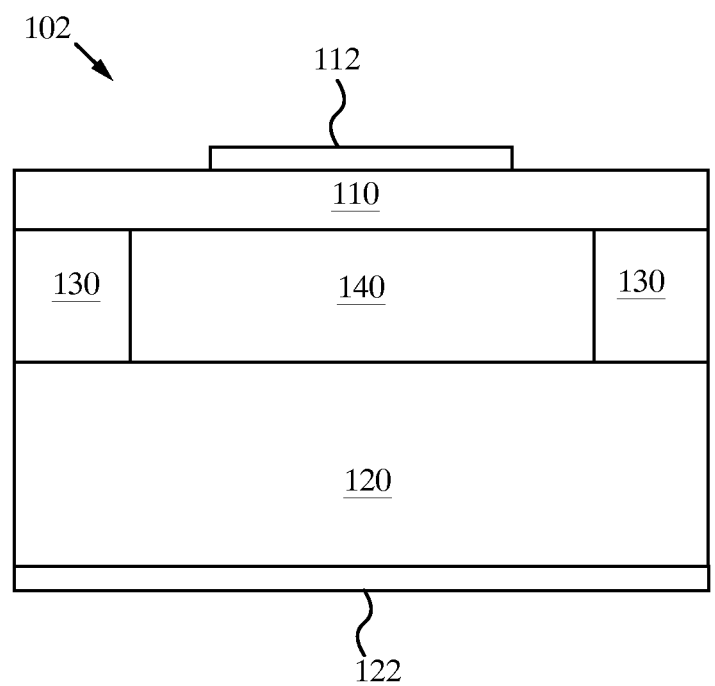
FIG. 2 shows a schematic cross-sectional view, of a sensor according to another embodiment of the invention.

FIG. 2 shows a cMUT sensor 102 having a functionalized membrane 110 that includes a first electrode 112. The substrate 120 contains a second electrode 122. Functionalized membrane 110 and substrate 120 are preferably thin membranes that are essentially parallel plate capacitors with a gap between the plates. In a preferred aspect of this embodiment, the conductive silicon wafer on which the functionalized membrane is fabricated, i.e. substrate 120, makes up one plate of the capacitor. A metal electrode 112 on top of the functionalized membrane 110 is the other plate of the capacitor. Functionalized membrane 110, which is supported by insulating support frame 130, is typically made of an insulating material, most commonly silicon, and is coated with the electrode 112. A low temperature oxide passivation layer may cover electrode 112 and functionalized membrane 110.

Figure 3:
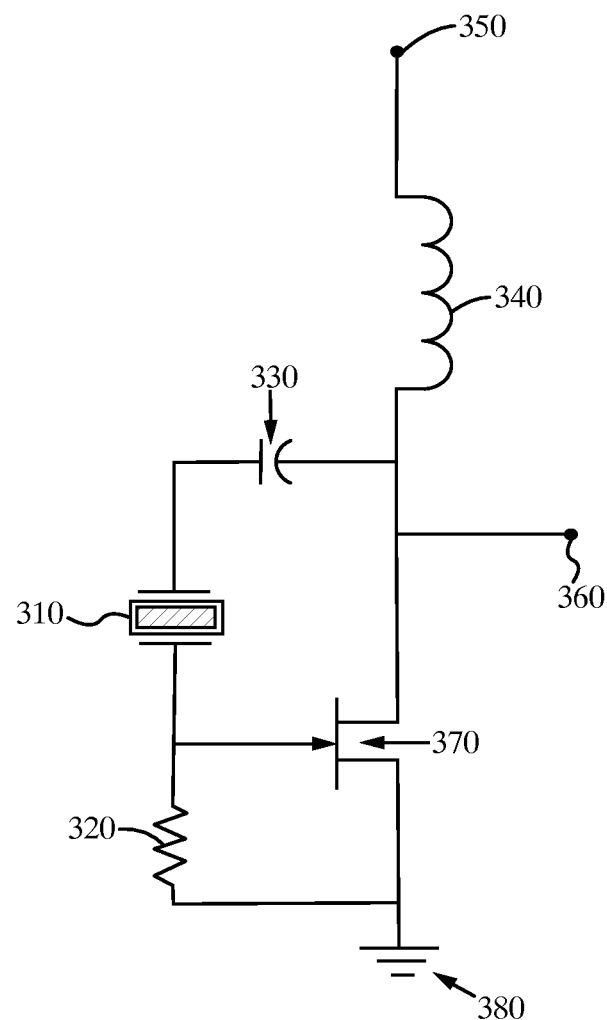
FIG. 3 shows an example of an electrical circuit for a sensor according to some embodiments of the invention.

FIG. 3 shows one embodiment of a circuit that is suitable for use with a resonant sensor. The circuit is one variation of an oscillator. The circuit includes a resonant sensor 310, resistor 320, capacitor 330, inductor 340, DC voltage source 350, sensor output 360, transistor 370, and connection to ground 380. Many other circuits are available to establish a resonant circuit using the sensor's resonant electrical input impedance (e.g., a Colpitts oscillator, Pierce oscillator, etc.). The output of these circuits is an approximately sinusoidal signal whose frequency is the measurable quantity of interest.

In some embodiments, the sensor is placed in the feedback loop of an amplifier and the gain of the amplifier is adjusted such that the circuit oscillates. The frequency of the oscillator is tuned by adjusting the DC bias that is applied to the sensor element. By controlling this DC bias the resonance or oscillation frequency is placed near the open circuit resonant frequency of the sensor. This may reduce the noise in the oscillator circuit, and hence increase the sensitivity of the sensor. When analyte adsorbs or binds to the receptor material on a resonating member of the sensor (e.g., the membrane 110 or a cantilever), its open circuit resonance frequency shifts, and this imparts a frequency shift in the oscillator circuit. By measuring the resonance frequency of the oscillator, one can estimate how much mass has deposited on the membrane 110.

Figure 4:
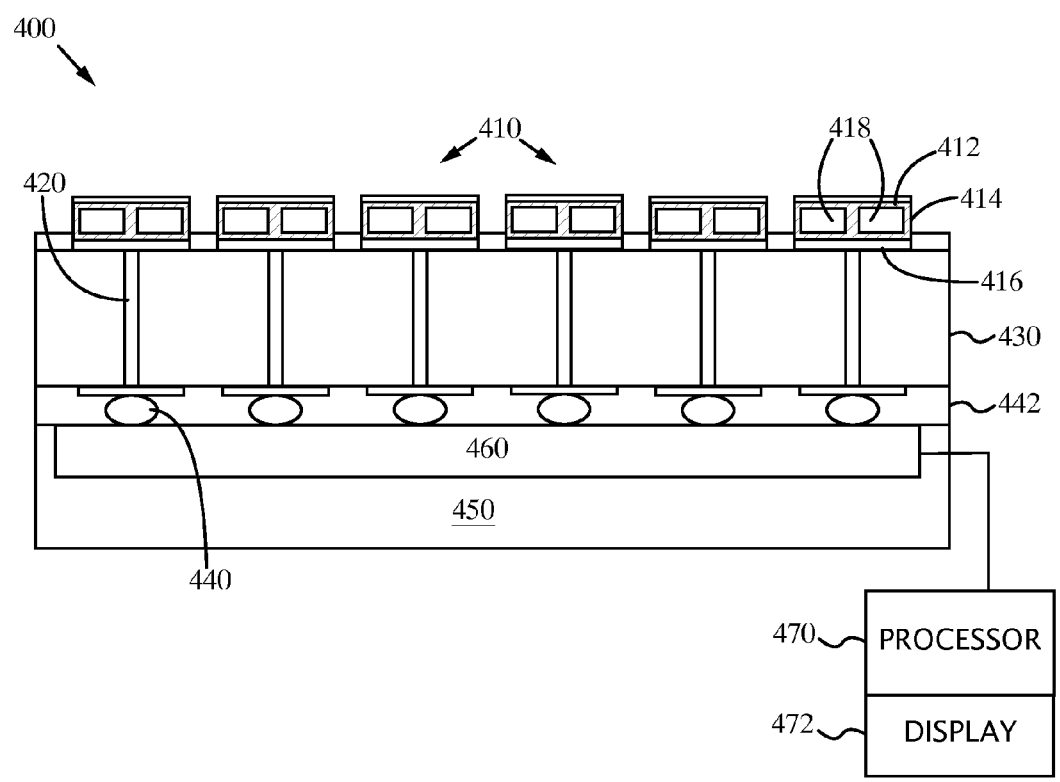
FIG. 4 shows a schematic, cross-sectional view of an array of sensors according to some embodiments of the invention.

FIG. 4 is a schematic cross-sectional view of a sensor device 400 containing an array of sensors 410 according to another embodiment of the invention. In this example, each sensor 410 contains two sensor elements, each of which has a membrane 412, support frame 414, substrate 416 and vacuum gap 418. The exterior surface of each membrane 412 is chemically functionalized. The sensors are designed for sensitivity to mass loading and stress loading by analytes adsorbed or bound to the membrane 412, and for matching into the electronic circuitry such as an oscillator that is used to detect the shift in the property of the membrane 412. Due to the functionalization of the membrane surface, analytes adsorb or bind to the surface of the membrane 412 when they are present in the environment or a sample to which the sensor is exposed. Consequently, the operational characteristics (e.g., impedance or resonance frequency) of the sensor will be altered, and this sensor response is detected.

The presence or amount of analyte(s) in a sample are measured by detecting the alteration of the operating characteristics of the resonating member (e.g., a membrane or cantilever). For example, an alteration in sensor characteristics can be detected by measuring the impedance of the sensor, or by measuring the change in the resonant frequency of the functionalized membrane 412. Interconnects 420 through wafer 430 provide electrical contacts from the sensors 410 to a wafer 450 with electronics layer 460. The interconnects 420 are separated from the electronics 460 by an underfill 442 and solder balls 440. (While solder bumps are shown in this figure, contacts may be made between wafer 430 and wafer 450 by any means known in the art, e.g. with an anisotropic conducting film).

The electronics layer 460 contains appropriate circuitry to drive and detect operational characteristics of the sensors 410, such as resonance frequencies of each membrane 412. Additional signal processing electronics or a processor 470 may be attached to the sensor electronics to further process the signals and to provide an indication of the presence or amount of analyte(s). For example, the indication of the presence or amount of analytes may be shown via the display 472 in communication (wirelessly or with wires) with the processor 470. The processor 470 receives data representative of the resonance frequencies (e.g., frequency output signals from the sensors 410) to determine the presence or amount of analyte(s). The processor 470 may be a microprocessor included with the device 400. Alternatively, processing functions may be performed in a separate processor or external computer in communication with the electronics layer 460. The external processor or computer receives data representative of the measured resonance frequencies and determines the presence or amount of analyte(s). Alternatively, multiple processors may be provided, e.g., providing one or more processors in the device 400 that communicate (wirelessly or with wires) with one or more external processors or computers.

Some processing of data can be done near the sensor. For instance, time averaging or multiplexing or digitization can be all processed in the vicinity of the sensor before being transmitted to a computer or a circuit board with a multiprocessor. Specific algorithms can be loaded in memory to perform the same functions one would in a digital computer and then drive displays where colored outputs can be used to indicate level of detection or hazard. As in many sensors deployed today, such as RF tags and implanted medical devices, it is possible to use RF antennas to couple and provide power to the sensor. Once a sensor is powered, it senses its function, and then the output of the sensor is re-radiated to a receiving antenna. In this fashion, the sensor device 400 can be passive and remotely addressed.

In some embodiments, a CMOS provides the circuitry to detect the mass loading of the membrane 412 either through an impedance change, by direct measurement, resonance frequency measurement, or any of various other means. The outputs of various sensors can be multiplexed, then a frequency counter can measure the frequencies. These outputs can then be digitized and stored and processed in a processor. The processor then can display the variation of the resonant frequency versus time and provide results of analysis of sensed species based, for example, on previously loaded models of sensitivity of multiple sensors to various chemicals.

The material properties and dimensions of the functionalized membranes 412 contribute to their resonant frequencies. In some embodiments, a DC bias is applied to the functionalized membranes 412 to maintain a very high electric field in the vacuum gaps 418. For instance, a silicon membrane 12 µm in diameter and 0.4 µm thick may resonate at a frequency of 42 MHz. In some embodiments, each sensor is used as the resonant tank of an oscillator circuit, where the resonant frequency shift indicates the amount of mass loading on the membranes 412. The sensitivity of such a resonator is defined as the ratio of the frequency shift over the frequency: $\Delta f/f = -\Delta m/2m$, where $\Delta m$ is the change in mass (i.e., mass of the species that adsorbs or binds to the sensor) over the total mass of the membrane.

In one embodiment, a resonance frequency response of the fundamental mode is supplemented by also measuring a series of higher harmonics of the membrane. The viscoelastic properties of the sensing layer (e.g., polymer) are influenced by absorption/adsorption. These properties are extracted through measuring the frequency dependence of the damping and the amplitude of higher order modes, and these measurements provide chemical information in addition to the resonance frequency. For instance, different mass loadings, polymer swelling and changes in the young modulus are detected through the amplitude and Q-factor. Off-resonance response may also provide information on viscoelasticity through the slope of the mechanical response. In some instances, the membrane in a sensor can be engineered to enhance the response at some harmonics.

In another embodiment, gases or liquids are exposed over a layer of polymer receptor material that adsorbs or binds the molecules of interest. The temperature of exposure will depend on the chemical desorption rate, and may be at room temperature or at lower temperatures depending on the molecule. After a set time, the sensor elements 410 may be heated either by thermal pulse or a linear programmed temperature ramp. During this heating, the molecules are desorbed and the change in resonant frequency and Q-factor shows a particular desorption profile similar to thermal desorption analysis commonly using spectrometric systems or gravimetrically (thermogravimetry). The temperature of desorption is an additional parameter that is sensitive to the chemical nature of the absorbent-absorbate interaction. After one thermal desorption cycle, a second subsequent cycle may be used to provide a reference calibration to be subtracted as a baseline from the first. The second thermal cycle reflects the thermomechanically induced change in resonance frequency.

Referring again to FIG. 2, the use of electrodes 112 provides a convenient method to heat the membrane 110. The small size and structure of the sensors ensures that low energy consumption, low thermal loads and fast (sub millisecond) response times can be achieved. The rapid response times aid resolution in the desorption profile. Temperature readouts of the sensors are also possible through integration of small thermocouples or the resistance of piezoresistive layers. The actual temperature profile during heating can provide information on phase transitions, heating or cooling effects. The sensor structure may be readily optimized to create an array of thermal sensor elements working on the bimetallic effect. Here temperature changes induce both changes in resonant frequency and static bending.

Sensor arrays may be configured, for example, as one-dimensional arrays of sensors or two-dimensional arrays of sensors. An advantage of a two-dimensional array is that an entire wafer may be populated with thousands of sensors. A one-dimensional array provides surface space, which may be used to integrate electronics side-by-side with the sensors. In some embodiments, a two-dimensional sensor array has electronics flip-chip bonded or fabricated under the sensor array. A sensor array with thousands of membranes may be useful in some embodiments for establishing the electrical impedance of the sensor, or for reducing the number of false alarms, if all the membranes in a sensor array are arranged to operate in parallel. If one sensor were to give a false indication, then the other sensors force a correct decision. Having thousands of sensors, many of which are functionalized in the same fashion, can also be used to reduce the false alarm rates and provide a more stable measurement of the presence of one or more analytes.

Figure 5:
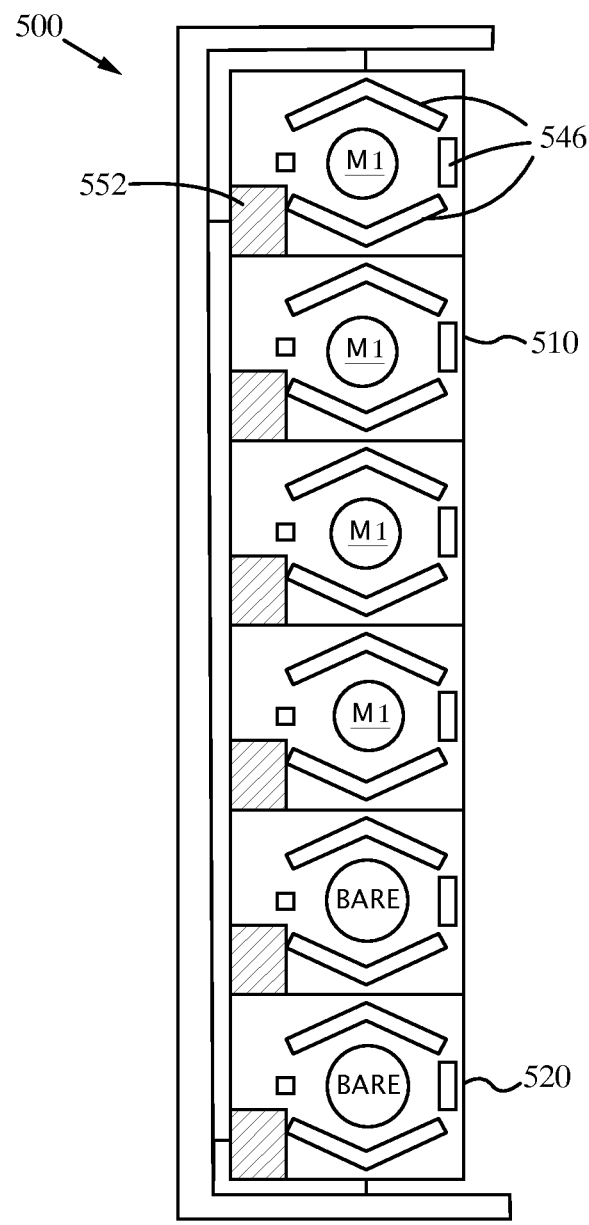
FIG. 5 shows a schematic, plan view of an array of sensors according to some embodiments of the invention.

FIG. 5 shows a sensor array 500 including six resonator sensors. To mechanically isolate each of the sensors or reduce crosstalk between the sensors, vertical trenches 546 may be added between each of the sensors. Each of the sensors may also include wire bond pad areas 552 for electrical connections. Sensor arrays may be made with any of various known cMUT fabrication techniques including: SOI bonding, sacrificial layer, surface or bulk micromachining, and silicon on insulator bonding. The sensor is preferably designed for maximum sensitivity while taking into consideration its mechanical loading and electrical interfacing into the integrated (or non-integrated) electronic circuitry. Sensors may be integrated with electronics in any of various known configurations including: flip chip bonding, elements constructed on top of electronics, or vice versa. The sensors may be fabricated with through wafer vias or trench isolated by etching through the back side using various well-known techniques for cMUT fabrication. Techniques suitable for fabricating such sensors are known in the art and are described, for example, in B. T. Khuri-Yakub and L. Levin, U.S. Pat. No. 5,828,394, which is incorporated herein by reference.

The resonating member of a sensor (e.g., a cMUT sensor) typically has a native silicon or silicon oxide surface. The bare surface of the resonating member typically does not interact with a surface molecule. It is usually an inert substrate to which a coated material adheres. The coated material is typically a polymer receptor material that adsorbs, binds or collects target analyte(s) in a sample. Analyte is detected by sensor responses (e.g., a change in resonance frequency of the resonating member) due to either increased mass from the analyte molecules or in some embodiments due to a change in one or more physical properties of the resonating member when exposed to the analyte. We have discovered that the nature of the substrate surface can have an effect on the reaction of the polymer receptor material to one or more analyte(s) and thus the sensor response. For example, coating the native sensor surface with a first layer of coating material (e.g., gold) prior to the application of the polymer receptor material to the gold surface may result in a sensor having a different response to target analyte(s) than does applying the same polymer receptor material to the native or bare substrate surface of the resonating member.

Surface modifications can be used to modify the functionality of the receptor material applied to the sensors, changing the sensitivity of the sensors to certain analyte(s). This enables simpler manufacturing processes that produce deliberate variations in the functionality of sensors in an array by simple surface modification with one or more inorganic materials applied and patterned on the resonating members of at least some of the sensors, while other resonating members may be left bare. The inorganic materials (e.g., metals or dielectric materials) may be deposited and patterned in processes that are relatively easy in micromachining, semiconductor and MEMS manufacturing. The same polymer receptor material may then be applied to the entire array (e.g., by spin-coating) to produce an array of sensors having resonating members with different functionalities for adsorbing or binding molecules of target analyte(s). This overcomes the need to deposit different polymer receptor materials on the individual resonating members, which is a difficult manufacturing problem.

Figure 9:
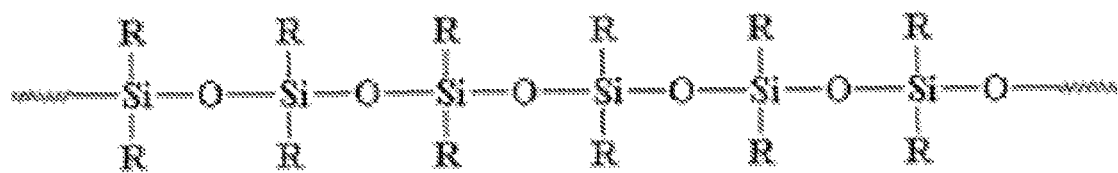
FIG. 9 is a schematic diagram illustrating Si—O—Si (Silicon Oxygen Silicon) links in a polymer.

Common polymers like Polyethylene include chains with a Carbon—Carbon backbone. Polysiloxanes are polymers where the backbone includes Si—O—Si (Silicon Oxygen Silicon) links, as illustrated schematically in FIG. 9. Choosing a specific molecular group to substitute "R" may afford special chemical properties, changing it from hydrophobic ($CH_3$) to hydrophilic (COOH), for example. Polysiloxanes can be linear, circular, or cross-linked depending on the choice of side groups and the addition of catalysts. By substituting one R with a branch containing a $NH_2$ group, a material called (3-Aminopropyltrimethoxysiloxane (AMO) can be formed which is sensitive to carbon dioxide ($CO_2$). By mixing AMO with other variants like Propyltrimethoxysiloxane (PTMS), different sensitivities and properties can be created.

It has been shown that AMO polymers react with carbon dioxide to form a reversible reaction. As a result, AMO and modifications thereof have been used as functional layers to enable certain transducers like QCMs, FET, and SAW devices as carbon dioxide detectors. We have shown that cMUT devices coated with AMO derived polymers are excellent carbon dioxide detectors. The basic chemistry underlying the $CO_2$ detection is an acid-base reaction between the $CO_2$ and $NH_2$ groups. Examples are described by Stegmeier et al. in "Optimization of the work function response of CO2-sensing Polysiloxane layers by modification of the polymerization" 2009 IEEE 978-1-4244-5335-1/09 pages 1742-1746, incorporated by reference herein. Another example is described by Zhou et al. in "Mass sensitive detection of carbon dioxide by amino group-functionalized polymers", Sensors and Actuators B 33 (1996) 188-193, incorporated by reference herein.

The nature of the substrate forming the resonating members of the sensors affects the response to carbon dioxide. When the sensor is coated with a gold layer and AMO is deposited on the underlying gold layer, the sensor surface is able to adsorb carbon dioxide. When AMO is coated on silicon without the gold layer, however, the AMO polymer is rendered insensitive to carbon dioxide and fails to substantially react to this analyte. Modification of the surface of the resonating element is sufficient to turn on or off the sensitivity of AMO polymer to adsorbing carbon dioxide without changing the polymer itself. For AMO polymer coated on the native silicon or oxide surface of the sensors, the AMO polymer retains its sensitivity for relative humidity (e.g., the polymer coating can bind or adsorb water molecules), but is no longer substantially responsive to carbon dioxide.

Surface modifications are used to modify the functionality of the polymer receptor material applied to the sensor array 500, changing the ability of individual resonating members to adsorb or bind a mass of certain analyte(s). This enables simpler manufacturing processes that produce deliberate variations in the functionality of sensors in the array 500 by simple surface modification with one or more easily patterned materials applied and patterned on the resonating members of at least some of the sensors, while other resonating members may be left bare. In this example, sensor array 500 has four sensors 510 having resonating members that are coated with a first layer of a coating material M1 (e.g., a metal such as gold) and two sensors 520 that have a bare or native silicon or silicon oxide surface.

In some embodiments, the array 500 is fabricated by depositing the first layer of coating material M1 on the native surface of the sensors 510. The coating material M1 is patterned (e.g., by lithographic techniques) such that it coats one or more resonating members of the sensors 510 while other bare sensors 520 are not coated with the coating material M1. Suitable coating materials include, but are not limited to, metals and dielectric materials. A polymer receptor material is then applied to all of the resonating members in the sensor array 500 (e.g., by spin-coating), so that one or more of the resonating members are coated with a combination of the polymer receptor material coated over the underlying material M1, and one or more other sensors 520 have the polymer receptor material coated on the native surface of the resonating member without an intervening coating material. The polymer receptor material in this embodiment is preferably an AMO derived polymer. In other embodiments, AMO is mixed with other variants like PTMS. Underlying materials (e.g., gold or aluminum oxide) may be deposited and patterned on individual resonating members in processes that are relatively easy in micromachining, semiconductor and MEMS manufacturing. The same polymer receptor material may then be applied to the entire array 500 (e.g., by spin-coating) to produce an array of sensors having resonating members with different functionalities for adsorbing or binding molecules of target analyte(s). This circumvents the need to deposit different polymer receptor materials on the individual resonating members of the sensors 510, 520, which is a difficult manufacturing problem.

Sensors may be functionalized with a polymer receptor material in various ways including, without limitation, electrospray, spin-coating, drop ejection, the use of ink jet techniques, spotter techniques, microfluidics, self-assembly, shadow masking coupled with the above, or spraying in vacuum through movable mask arrays. One may select and test an optimum mixture of polymers as the receptor material to generate a robust signature pattern for an analyte. Polymer receptor materials respond to gas-phase analytes in seconds to tens of minutes. The selection of a polymer is preferably optimized to fit the mechanical properties of the resonating members of the sensors (elasticity, density, thickness, etc.), so that detection time is minimized and sensitivity is maximized. In some embodiments, neutral polymer gels may be used as carriers for receptor materials. Using this method, a variety of compounds that do not form stable films themselves can be applied through drop or spin-coating.

The polymer receptor material may be specific or a non-specific receptor with respect to one or more target analytes. Target molecules can react with the sensors with a pattern of masses adsorbed or bound to the resonating members, which pattern is specific for each target. The observed pattern can be used to identify a target analyte that has been previously characterized so that its pattern is known. If more than one target analyte is present in a sample (a mixture), then the individual known patterns can be deconvolved to separate the individual analytes. The degree of response can be used to quantify the amount of a particular analyte, e.g. the ppm concentration of a specific gas. If a previously uncharacterized analyte is present, an unknown pattern of masses may be detected. In this case, while a specific identification and quantification of the unknown analyte may not be possible, some general properties of the unknown may be determined from the nature of its pattern. The formation of a spatial pattern of masses on the sensors sorts molecules according to the degree of affinity. So even if the detected analyte is not known, the pattern of masses in the sensor array allows assignment of the analyte to a broader category.

Figure 6A:
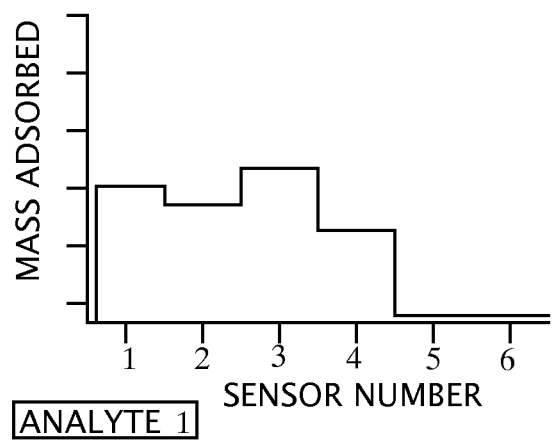
FIGS. 6A-6B are graphs showing masses adsorbed on sensors in an array according to some embodiments of the invention.
Figure 6B:
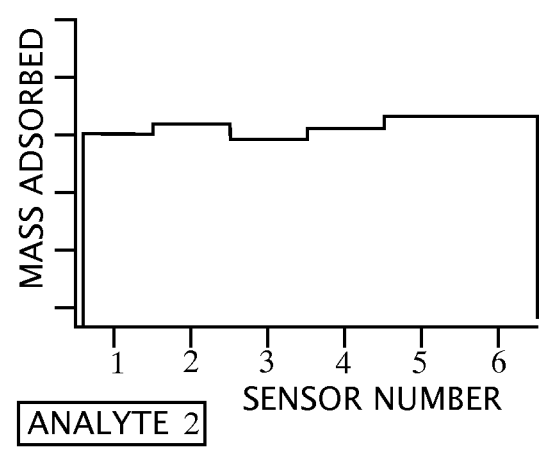

FIGS. 6A-6B are graphs showing patterns of masses adsorbed on each functionalized sensor for target analytes. In this example, the target analytes are carbon dioxide and water (e.g., to determine relative humidity). Masses of a target molecule like carbon dioxide are adsorbed on sensors 1-4 (having a gold layer and a polymer receptor material applied over the gold), as shown in FIG. 6A. Sensors 5-6 (which have the polymer receptor material applied to the native sensor surface without gold) do not adsorb masses of the carbon dioxide molecules. FIG. 6B is a graph showing masses of water molecules binding to each of sensor numbers 1-6.

Figure 7:
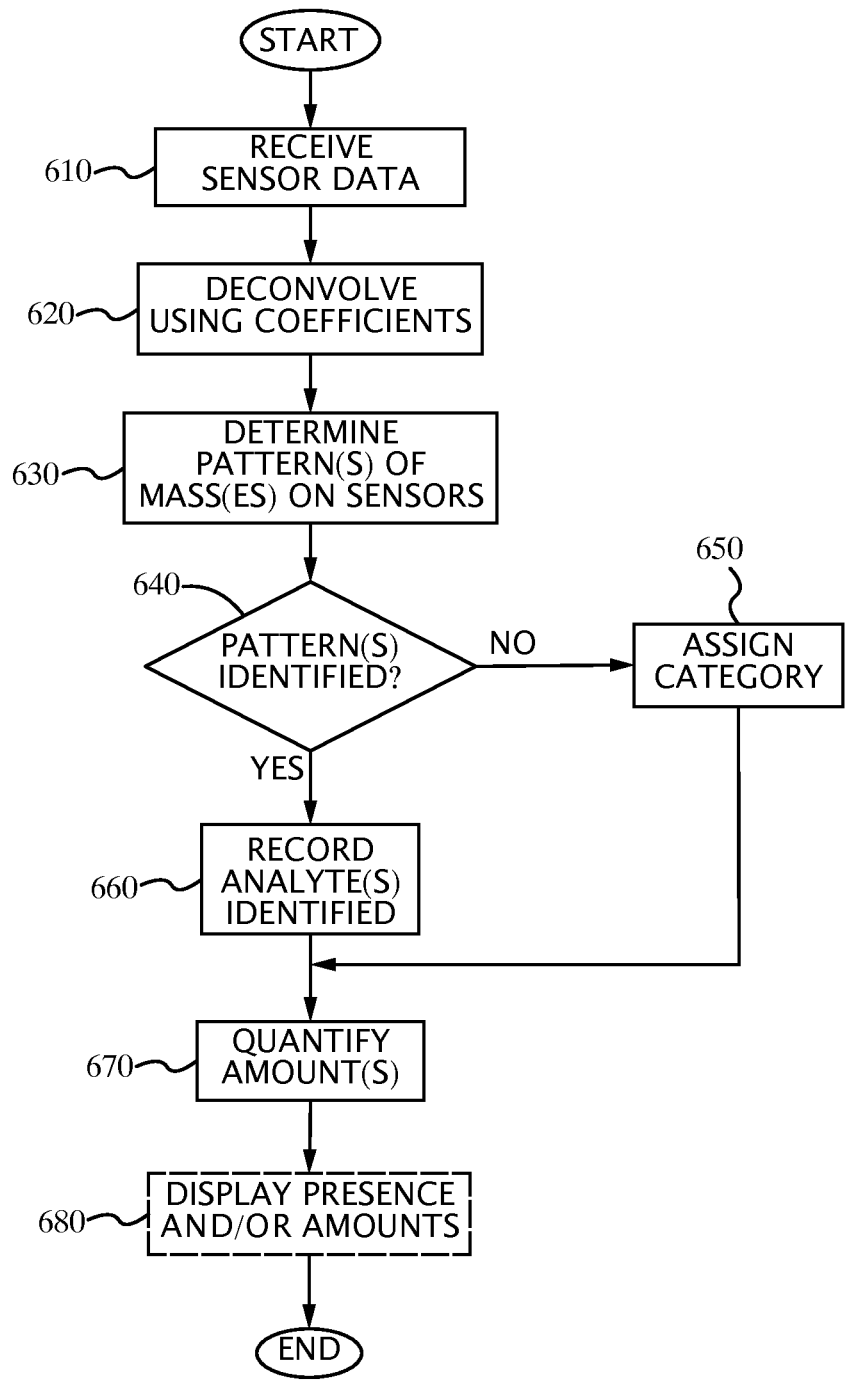
FIG. 7 is a flow chart showing steps of a method employing at least one processor to determine the presence or amounts of one or more analytes according to some embodiments of the invention.

FIG. 7 is a flow chart showing steps of a method employing at least one processor to determine the presence or amount(s) of one or more analytes, according to some embodiments. In step 610, a processor receives data representative of the sensor responses (e.g., changes in positions or resonance frequencies of the functionalized sensors in response to one or more analytes). In step 620, the processor deconvolves or de-convolutes the data using coefficients. This step can be performed with a set of equations, or more generally by a matrix. In a simple form, let A be the signal amplitude of sensor 1 indicating the sensor response, and X the quantity of unknown target analyte adsorbed on the sensor 1. We can describe the dependence of amplitude A and unknown quantity X by a linear relationship and a coefficient $a_x$ so that $A=a_x X$. If there is more than one target analyte on sensor 1, such as analyte X and Y, then $A=a_x X+a_y Y$.

If we now add a second sensor with a different polymer or affinity $b_x$ and $b_y$, and assume that the second sensor is exposed to the same quantities X and Y of analytes (since the sensors are adjacent or proximate), then we measure a different value B with second sensor and solve two equations with two variables:

$$A = a_x X + a_y Y \quad (1)$$

$$B = b_x X + b_y Y \quad (2)$$

More generally, if we know the matrix of coefficients $a_{ij}$, then we can determine the amounts of multiple analytes $X_j$ if we have measured the amplitudes of I sensors $A_i$ using the vector product (equation 3):

$$A_i = a_{ij} X_j \quad (3)$$

If the number of sensors is greater than or equal to the number of targets, the equation can be solved. For example, for a thirty-two sensor chip up to thirty-two different target molecules can be determined. In practice however, one may choose some redundancy to improve accuracy and use thirty-two sensors to target a more limited set of eight analytes. An array of sensors is preferably calibrated to determine the values of the matrix $a_{ij}$, with known analytes of interest $X_j$. The calibration data is stored either in the sensor array device or in a separate processor where the signals are analyzed.

In step 630, the processor determines respective patterns of masses on the sensors for each analyte (represented in the graphs of FIGS. 6A-6B). In decision step 640, it is determined if one or more of the patterns is identified as representative of a known target analyte. If the pattern is not identified, then the unknown analyte is assigned to a broad category based on its pattern of masses on the sensors, in step 650. If the pattern is identified, then the identified analyte is recorded, in step 660. In step 670, the degree of response is used quantify the amount of one or more analyte(s), e.g., the ppm concentration of a specific gas. In optional step 680, the presence or amounts of the detected analyte(s) are displayed.

Figure 8:
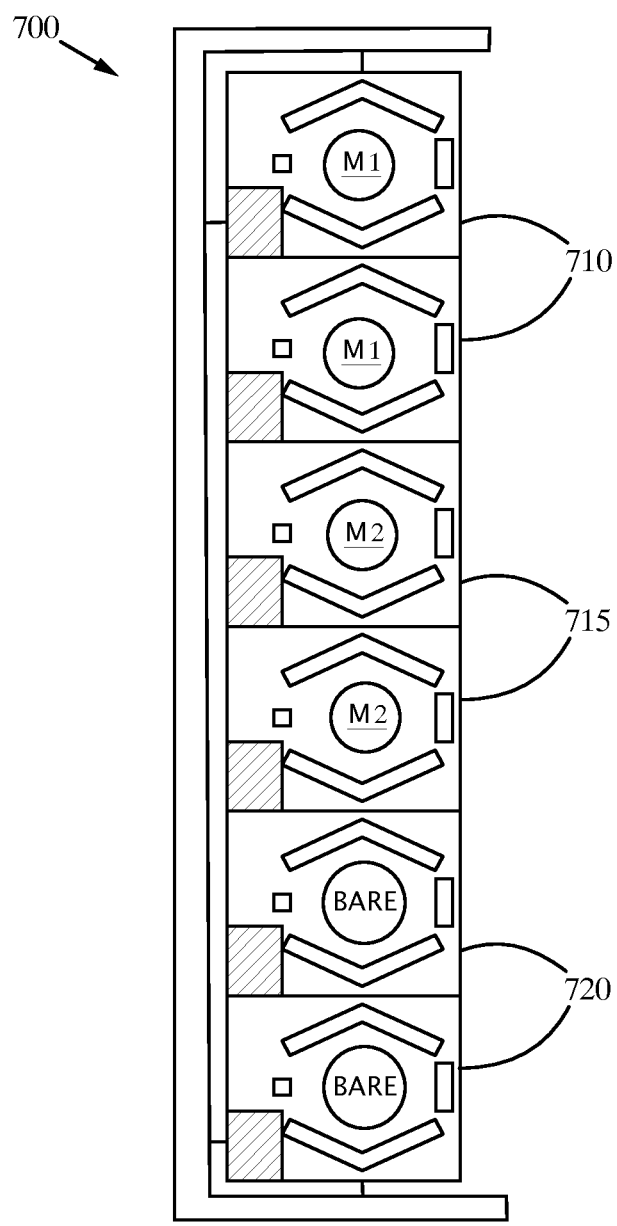
FIG. 8 shows a schematic, plan view of a sensor array according to another embodiment of the invention.

FIG. 8 shows a schematic, plan view of a sensor array 700 according to another embodiment of the invention. The array 700 has two sensors 710 having resonating members that are coated with a first layer of a first coating material M1. Similarly, two of the sensors 715 have resonating members that are coated with a first layer of a second coating material M2 that is different than the first coating material M1, while the sensors 720 remain bare. Suitable coating materials include, but are not limited to, metals and dielectric materials. In some embodiments, the first coating material M1 is gold and the second coating material M2 is aluminum oxide. In some embodiments, the layers of coating materials or "pre-coatings" M1 and M2 are not inert, but interact with a polymer receptor material applied to the array 700, e.g., by spin-coating the polymer receptor material onto the array 700 such that it coats all of the resonating members.

Utilizing the polymer receptor material in combination with the pre-coating M1, the pre-coating M2, and the native or bare substrate surface (typically silicon or silicon oxide) provides an easier method to manufacture the sensor array 700 having respective sensors 710, 715 and 720 with three different materials underlying the coating of the polymer receptor material, and thus three different functionalities for adsorbing or binding molecules of target analyte(s). It is simpler to apply pre-coatings M1 and M2 to specific sensors and then apply a single polymer receptor material to an entire sensor chip. This is particularly true if the pre-coatings are materials that can be applied to individual sensors at the wafer level, e.g. metals deposited in a lithographic process or dielectric materials. These pre-coatings might be able to endure downstream process steps (e.g. dicing and packaging), allowing a final relatively simple application to the entire chip of a potentially less robust polymer receptor material. Thus, one device may easily be fabricated with N sensors having up to N different pre-coating materials underlying a coating of the same polymer receptor material. At least one processor may be employed with sensor array 700 to determine the presence or amount of the analytes in a sample exposed to the sensors 710, 715 and 720, previously described with reference to FIG. 7.

A sensor array may optionally include at least one background or reference sensor to provide a reference signal. The reference sensor preferably includes a non-functionalized or passivated membrane instead of a functionalized membrane. The number of sensors in the array that will be used as reference may be determined experimentally. Typically, it is expected that 1% to 50% of the sensors in the array will be non-functionalized and used as a reference.

Sensor arrays may be used in liquid, gas, or vacuum. Operational temperatures range from cryogenic to high temperatures, depending on the limits of the receptor materials. For operation in immersion, the cells in the cMUT or pMUT or mMUT, or whatever variation, could be made with cells that are distant from nearest neighbors, by design, to provide a narrow band operation. In one embodiment, sensor arrays may be connected down stream from a separation system (such as used in chromatography or gel electrophoresis) to detect specific patterns in complex mixtures of liquids.

In operation, a sensor array can be mounted on a wall, ceiling or other portion of a fixed structure, incorporated into a hand-held device (e.g., a cell phone), or mounted on a moving vehicle, to name just a few methods of exposing the sensor array to a sample. Depending on the specific application, it may be used with or without active circulation of analyte-containing gas or liquid over the sensors to increase exposure of the sensor to analytes (e.g., chemicals) in the environment. The small dimensions of the sensor arrays readily facilitate the integration of the sensor at even millimeter distances from the sampling inlet.

In liquids, the sensor arrays can be incorporated into submarines, ships, divers' handheld devices or parts. Likewise, drinking water, toilets and anywhere liquids are used can be readily monitored or tracked. In another mode of operation, sensor arrays may be used as part of microfluidic devices enabling the detection of small (μL) micro liter volumes. The use of artificial Q enhancements can be applied to increase the sensitivity of the apparatus. Sensor arrays may be integrated with other devices and systems such as, for example, gas handling systems or self-calibrating systems.

It will be clear to one skilled in the art that the above embodiments may be altered in many ways without departing from the scope of the invention. Many different permutations or arrangements may be used to realize the device and method of the invention. For example, sensor arrays containing multiple sensors may have membranes with different resonant frequencies. A membrane operating at low frequency yields a sensor more sensitive to stress on the membrane, whereas a membrane operating at high frequency gives a sensor that is more sensitive to mass loading. Combining various operating frequencies in one sensor thus provides a sensor with a greater versatility.

In some embodiments, the thickness of the polymer receptor material coated on the sensors may be varied. For example, the speed of the spin coating can be varied, thereby varying the thickness of the deposited receptor material. This variation in the amount or thickness of polymer receptor material on each sensor establishes one more pathway to provide redundancy and enhance the accuracy of the sensor array (fewer false positives). In some embodiments, various other types of receptor materials may be doped or functionalized. These materials include, for example, polymers (co-polymers, bio-polymers), sol gels, porous materials (silicon, zeolite, etc.), DNA, RNA, proteins, cells, bacteria, carbon nanotube arrays, catalysts including metals to enzymes, nanoclusters, and organic and inorganic materials including supramolecules, metal-organic complexes, and dendritic materials.

In some embodiments, electronics are integrated with sensor arrays, where multiple sensors are attached in parallel, and sensors are operated at different frequencies so that one output line may be used. For this purpose, different sensors may be built and operated at different frequencies. For example, a row of sensors can be made to resonate from 45 MHz to 55 MHz in 0.1 MHz intervals. Principles of dense wavelength division multiplexing (DWDM) may be used in such devices. By altering the diameter of resonating elements, it is possible to change the frequency of operation. Having sensors operating at multiple frequencies can have advantages in electronic integration in transmitting information at different frequencies on the same channel, and in separating the influence of stress and mass loading on the shift in resonant frequency of a resonator.

In one embodiment, large arrays of sensors may be used to develop a physics/chemistry-based model to extract unique inversion for single element identification using multiple functional agents. In particular, collecting data about the sensitivity to certain species by different functionalizing chemistries allows the development of a model to relate the outputs of the multiple sensors to the different species with higher accuracy.

Accordingly, the scope of the invention should be determined by the following claims and their legal equivalents.

What is claimed is:

1. A device comprising:
   a) at least first and second resonator sensors, wherein the first sensor includes a first resonating member having a first surface comprising a receptor material coated over a first underlying material, the second sensor includes a second resonating member having a second surface comprising the receptor material coated over a second underlying material that is different than the first underlying material, and the first underlying material, the second underlying material and the receptor material are selected such that the first resonating member, having a combination of the receptor material and the first underlying material, has a different ability to adsorb or bind a mass of one or more analytes than does the second resonating member having a combination of the receptor material with the second underlying material; and
   b) at least one detector arranged to detect responses of the sensors when the sensors are exposed to a sample potentially containing one or more of the analytes.

2. The device of claim 1, wherein the first underlying material comprises gold and the second underlying material comprises silicon, silicon oxide or aluminum oxide.

3. The device of claim 1, wherein the receptor material comprises 3-Aminopropyltrimethoxysiloxane (AMO).

4. The device of claim 1, wherein the receptor material comprises a mixture of 3-Aminopropyltrimethoxysiloxane (AMO) and Propyltrimethoxysiloxane (PTMS).

5. The device of claim 1, further comprising a third resonator sensor that includes a third resonating member having a third surface comprising the receptor material coated over a third underlying material that differs from the first and second underlying materials, wherein the receptor material and the underlying materials are selected such that the first, second and third resonating members have different functionalities for adsorbing or binding molecules of one or more of the analytes.

6. The device of claim 1, wherein the underlying materials comprise different metals.

7. The device of claim 1, wherein the sensor responses comprise changes in resonance frequencies.

8. The device of claim 1, further comprising at least one processor in communication with the detector for receiving data representative of the sensor responses, wherein the at least one processor is programmed to determine the presence or amount of the analytes according to the data.

9. The device of claim 1, wherein each of the resonator sensors comprises a capacitive micromachined ultrasound transducer (cMUT).

* * * * *